United States Patent
Hampp et al.

(10) Patent No.: US 6,887,269 B1
(45) Date of Patent: May 3, 2005

(54) OPHTHALMOLOGIC IMPLANT

(75) Inventors: Norbert Hampp, Schillerstrasse 10, 35287 Amöneburg-Rossdorf (DE); Walter Heitz, Kirchhain (DE); Andreas Greiner, Marburg (DE); Lutz Hesse, Marburg (DE)

(73) Assignee: Norbert Hampp (DE)

( * ) Notice: Subject to any disclaimer, the term of this patent is extended or adjusted under 35 U.S.C. 154(b) by 0 days.

(21) Appl. No.: 10/129,954
(22) PCT Filed: Nov. 17, 2000
(86) PCT No.: PCT/EP00/11477
§ 371 (c)(1), (2), (4) Date: Jul. 9, 2002
(87) PCT Pub. No.: WO01/35867
PCT Pub. Date: May 25, 2001

(30) Foreign Application Priority Data

Nov. 19, 1999 (DE) .......................... 199 55 836

(51) Int. Cl.$^7$ .................................. A61F 2/14
(52) U.S. Cl. ................... 623/6.57; 623/6.16; 623/6.56
(58) Field of Search ................ 623/4.1, 5.16, 623/6.11, 6.16, 6.56, 6.57, 6.62

(56) References Cited

U.S. PATENT DOCUMENTS

| 4,731,080 | A | * | 3/1988 | Galin | 623/6.57 |
| 5,554,187 | A | * | 9/1996 | Rizzo, III | 623/6.16 |
| 5,576,345 | A | | 11/1996 | Mansson et al. | |
| 6,340,588 | B1 | * | 1/2002 | Nova et al. | 435/287.1 |
| 6,423,818 | B1 | * | 7/2002 | Matsuda et al. | 528/354 |

FOREIGN PATENT DOCUMENTS

| WO | WO 97/06838 | 2/1997 |
| WO | WO 99/52570 | 10/1999 |

OTHER PUBLICATIONS

German Patent Office Examination Report DE 199 55836.1.

* cited by examiner

*Primary Examiner*—Corrine McDermott
*Assistant Examiner*—William H Matthews
(74) *Attorney, Agent, or Firm*—Rothwell, Figg, Ernst & Manbeck, P.C.

(57) ABSTRACT

An ophthalmologic implant for the prophylaxis or treatment of capsule opacification after implantation and completion of wound healing of a synthetic lens is described. This treatment can be repeated if necessary.

15 Claims, 3 Drawing Sheets

OPHTHALMOLOGIC IMPLANT

DESCRIPTION

Figure 1:
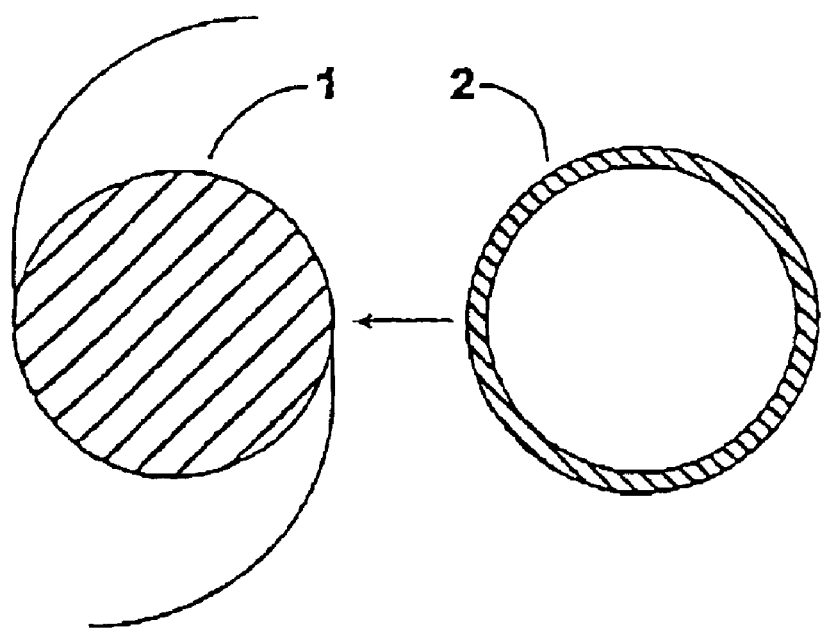

The invention concerns an ophthalmologic implant made of a polymeric material which is preferably itself in the form of an intraocular lens or is used as an auxiliary equipment for intraocular lenses. The implant is used in particular for the prophylaxis or/and treatment of capsule opacification after the implantation of a synthetic lens and after the completion of wound healing. The treatment can be repeated if necessary.

The medical term for an opacified lens is a cataract. If a cataract occurs in the natural lens this is referred to as a primary cataract. If an opacification occurs after explantation of the natural lens and implantation of a synthetic lens, it is referred to as a secondary cataract or as "cataracta" (after-cataract). The English term "posterior capsule opacification" or the abbreviation PCO is frequently used in the terminology.

A cataract is usually treated by surgically removing the opacified lens and implanting an allogenic intraocular lens in the remaining lens capsule sac. This surgical intervention is one of the most common ophthalmic operations. However, it is usually not possible to completely clean away remaining lens epithelial cells from the capsule sac. Cells often remain at the equator of the lens sac which proliferate and migrate centrally from there which later leads to an opacity in the region of the capsule sac i.e. the formation of a secondary cataract. This requires a surgical intervention which is expensive and a burden for the patient, and has inherent risks (e.g. retina detachment).

The development of a secondary cataract is a particular problem in children and young adults. In such cases the regeneration rate of the lens epithelial cells is so pronounced that a strong opacification already occurs in some cases after a few weeks. The development of a secondary cataract not only impairs vision but may require further surgical and diagnostic measures such as laser coagulation or detailed examinations of the retina.

The number of implanted intraocular lenses has steadily increased in recent years. At present it is estimated that 400,000 intraocular lenses are implanted per year in Germany in cataract operations. After operations that are without complications and an uneventful postoperative healing process, it can be expected that an impairment of vision caused by a secondary cataract due to the proliferation of residual lens epithelial cells will occur again in a considerable number of patients.

Various methods have been employed to prevent this proliferation.

U.S. Pat. No. 5,576,345 describes the use of taxol and taxol derivatives to prevent secondary cataracts. For this purpose taxol or a taxol derivative is administered into the intraocular area according to U.S. Pat. No. 5,576,345 in which case the intraocular lens can serve as a carrier for the active substance. The use of an immobilized, photochemically activatable component to achieve a depot effect is not taken into consideration.

WO 99/52570 describes a coated intraocular lens comprising a substrate material and a coating which is intended to reduce the risk of opacification after implantation of the synthetic lens. Hydrophobic arylacryl monomers are used as the coating material.

WO 97/06838 concerns an intraocular lens on which a carrier medium with embedded active substances is applied.

Another approach is to completely remove lens epithelial cells from the capsule sac during the operation (R. C. Humphry, E. G. Davies, T. J. C. Jakob, G. M. Thompson: The human anterior lens capsule—an attempted chemical debridement of epithelial cells by ethylenediaminetetraacetic acid (EDTA) and trypsin. Br. J. Ophthalmol. 72 (1988) 406–408; O. Nishi, K. Nishi, M. Hikida: Removal of lens epithelial cells by dispersion with enzymatic treatment followed by aspiration. Opthalmic. Surg. 22 (1991) 444–450).

However, when lens epithelial cells are removed from the capsule sac during the operation, it is not possible to surgically ensure that all epithelial cells have been completely removed. It can also not be accomplished by the additional use of chemical agents. The use of aggressive chemical reagents is out of the question for medical reasons since it would not be possible to preclude damage to the capsule sac or neighbouring tissue.

In addition, it was attempted to inhibit proliferation of lens epithelial cells by modifying the intraocular lens surface and by using alternative intraocular lens materials, respectively (G. Duncan, I. M. Wormstone, C. S. C. Liu, J. M. Marcantonia, P. D. Davies: Thapsigargin-coated intraocular lenses inhibit human lens cell growth. Nature 3 (1997) 1026–1028; R. J. Siezen, C. M. Coppin, G. B. Benedek: Process for preventing or reversing cataract formation using protein modification reagents. U.S. Pat. No. 4,665,089 (1987); L. Hesse, L. Freisberg, H. Bienert, H. Richter, C. Kreiner, C. Mittermayer: "Verminderung des Nachstars durch Plasmaätzung von Intraokularlinsen", Ophthalmologe 94 (1997) 821–825).

Intraocular lenses which have a modified surface or are made of modified materials which are intended to permanently prevent overgrowth with epithelial cells are currently being evaluated. However, this method alone cannot prevent a secondary cataract. The lens epithelial cells can also grow on the inner side of the capsule sac and then migrate centrally. Furthermore measures that are permanently toxic to the epithelium impair wound healing after implanting a synthetic lens.

Another method comprises the use of proliferation-inhibiting or cytotoxic substances in the capsule sac (D. W. Cash: Method of inhibiting cataracts by topical application of a 2-substituted 1,2-benz-isoselenazol-3(2H)-one. U.S. Pat. No. 4,778,815 (1988); J. M. Emery, R. Y. Chan: Mitotic inhibitors preventing posterior lens capsule opacification. U.S. Pat. No. 4,657,930 (1987); J. M. Ruiz, A. Medrano, J. L. Alio: Inhibition of posterior capsule opacification by 5-fluorouracil in rabbits. Ophthalmic. Res. 22 (1990) 201–208).

However, the use of proliferation inhibitors or cytotoxic substances or related pharmaceutical agents in the capsule sac impairs wound healing after an operation.

Data on the incidence of secondary cataracts vary and essentially depend on the follow-up period. Despite the said measures, such as modified surgical techniques and modified lens design, the incidence of secondary cataracts is 20–50% within a time interval of 2–5 years (D. J. Apple, K. D. Solomon, M. R. Tetz, El. Assia, E. Y. Holland, V. F. C. Legler, J. C. Tsai: Posterior capsule opacification. Surv. Ophthalmol. 37 (1992) 73–116; C. Ohadi, H. Moreia, P. McDonell: Posterior capsule opacification. Curr. Opin. Ophthalmol. 2 (1991) 46–52).

This shows that it is not yet possible to effectively prevent the formation of a secondary cataract.

Moreover all known methods have the disadvantage that if a secondary cataract forms, it is not possible to repeat the therapeutic measure or to repeat the application at a stronger dose without having to surgically open the eye.

The proliferation of lens epithelial cells is a complicated process, the exact mechanism of which is presently unknown. Apart from a loss of contact inhibition, mediators of inflammation and other factors influence the development of a secondary cataract. Drug treatment of a secondary cataract is impeded by the fact that only a few substances can be taken up into the interior chamber after being applied dropwise onto the cornea. In addition the intraocular lens impairs the exchange of chamber water in the capsule sac. The chamber water volume must be regarded pharmacologically as an independent compartment.

As a consequence the application of an inhibitory substance to the anterior chamber has to take place during or at the end of the lens implantation operation. However, the active substances that come into consideration all have an undesired inhibitory effect on post-operative wound healing.

Hence an object of the invention was to provide an ophthalmologic implant such as an intraocular lens or an auxiliary equipment for existing intraocular lenses which can be used to avoid the complications after a cataract operation described above and can permanently suppress the proliferation of lens epithelial cells.

This object is achieved according to the invention by an ophthalmologic implant for the prophylaxis or/and treatment of capsule opacification after implantation of a synthetic lens which is characterized in that it is composed of a polymeric material and comprises, at least in certain areas, a chemical component in an immobilized form from which a pharmaceutical substance can be released by photochemical activation. The active substance preferably has a cytotoxic effect. The released active substance particularly preferably has a toxic effect on epithelium and in particular on lens epithelium.

The implant according to the invention enables the desired drug effect, e.g. a cytotoxic effect and in particular toxic effect on epithelium, to be not activated immediately after the operation but as required at a later time e.g. at the earliest after completion of wound healing, and optionally allows reactivation of the effect several years after the implantation. According to the invention the active substance e.g. a substance which has a toxic effect on epithelium, is not permanently active and thus not already active immediately after the implantation which would impair wound healing. Rather the ophthalmologic implant contains the pharmaceutical substance in an inactive form. Hence the active substance can be applied in a pharmacologically inactive form during the cataract operation by implantation of a drug depot. Hence the implant contains a photoactivatable depot of active substance. The release of active substance can then be non-invasively induced by photochemical activation after completion of wound healing. The activation releases the previously fixed active substance into the small chamber water volume in amounts suitable to achieve therapeutically relevant concentrations at this site in order to for example kill lens epithelial cells that have formed and prevent the growth of new lens epithelial cells.

A particular advantage is that the therapeutic effect can be controlled and improved by a staggered, multiple, non-invasive release of active substance.

Another advantage is that this treatment can be carried out as an ambulant treatment in all ophthalmic centres with laser equipment and hence surgical (laser) intervention with destruction of the posterior capsule is no longer necessary.

The active substance can already be specifically released in the initial stage of a capsule opacification e.g. at the first occurrence of overgrowth of the implanted lens with epithelial cells which can for example be determined with the aid of a microscope. This enables the capsule opacification to be treated in an initial stage i.e. before the vision of the affected person is significantly impaired.

The implant according to the invention is preferably used to treat capsule opacification. However, it is also possible to use the implant according to the invention as a preventive measure for prophylaxis by releasing at least some of the active substance after wound healing but before capsule opacification occurs in order to for example kill any remaining cells, that were not removed during the operation, and in particular lens epithelial cells.

The ophthalmologic implant according to the invention is preferably an intraocular lens or an auxiliary equipment for an intraocular lens. In order to prevent or treat capsule opacification after implantation, the implant is made of a polymeric material which contains, wholly or in zones, a chemical component is an immobilized form from which a pharmaceutical substance is released by photochemical activation which is preferably cytotoxic and preferably has a toxic effect on epithelium and in particular inhibits or suppresses the proliferation of lens epithelial cells or kills lens epithelial cells that may be present.

In a first embodiment the ophthalmologic implant is an intraocular lens without any necessary auxiliary equipment. The intraocular lenses according to the invention are either completely or only partially, e.g. only in individual zones as a toroid-shaped marginal zone, manufactured from the polymeric material according to the invention. Another embodiment is that an intraocular lens manufactured from a polymer which is not loaded with active substance is coated with a thin layer of the polymer loaded with active substance according to the invention.

Another embodiment comprises auxiliary equipments for conventional intraocular lenses. The auxiliary equipment is advantageously composed of a separate element which itself does not have the function of a lens but is implanted together with a conventional intraocular lens e.g. a toroid-shaped polymeric co-implant.

The ophthalmologic implant according to the invention can basically comprise a chemical component from which any pharmaceutical substance that is advantageous for the eye can be released by photochemical activation. The chemical component in an immobilized form is preferably able to release a pharmaceutical substance which has a cytotoxic effect and in particular a toxic effect on epithelium. Other active substances that can be immobilized in an inactive form for example comprise antibiotics such as antimicrobial substances which are preferably active against common pathogens that occur in the eye, anti-inflammatory materials such as corticosteroids and non-steroidal anti-inflammatory agents and antiviral (e.g. Ganciclovir) or fungicidal agents. It is also possible to immobilize active substances such as hormones or enzymes such as anti-fibroblast growth factor or active substances which inhibit a proliferative vitreoretinopathy or a tissue fibrosis. Other suitable active substances for example comprise antibodies e.g. against the transforming growth factor $\beta$ and inhibitors of for example peptide promoters, inhibitors of growth factors and kinase inhibitors. The ophthalmologic implant according to the invention can contain one or any desired mixtures of several of the above-mentioned active substances in an immobilized form.

The active substance can be located on the surface or/and in the interior of the polymeric material. According to a preferred embodiment the active substance is covalently coupled to the polymeric material or to a polymeric component thereof via photochemically cleavable linker molecules. The linker molecules are preferably selected from the group comprising cinnamic acids, coumarins or derivatives thereof.

In an alternative embodiment the active substance is incorporated into the polymeric material of the intraocular lens or auxiliary equipment in the form of photocleavable oligomers or polymers, and it is fixed for example by mechanical enclosure or/and by covalent cross-linking.

Another alternative for integrating the active substance is to incorporate macromolecular conjugates of the active substance and one or more auxiliary substances, where the auxiliary substances serve to cross-link the active substance and improve the solubility of the macromolecular conjugate in the polymeric material and contain photocleavable groups.

Another alternative solution is to mix a photoactivatable precursor of an active substance with the polymeric material in a nanodispersed form where the average particle size is <1 µm and preferably <500 nm.

The immobilized chemical component is itself pharmaceutically inactive. The chemical component is preferably a form of the active substance that can be immobilized on the implant. Since the active substance can develop its desired effect, e.g. a toxic effect on epithelium, only when it is in direct contact with the epithelial cells, it is inactivated by the immobilization.

In a further preferred embodiment an inactive precursor of the active substance is present in the form of a conjugate which contains the active substance bound to other molecules or/and in the form of a polymer or oligomer of several active substance molecules in which the active form of the active substance is obtained by release of individual molecules of the active substance.

According to the invention the active substances can be specifically activated at any desired time by photochemical release. Hence it is possible to incorporate the active substance in an inactive form as a depot and not activate it until a desired later time.

Thus it is for example possible to firstly wait until the wound healing is finished after an operation before an effect, e.g. a toxic effect on the epithelium, is activated. Furthermore it is possible to specifically activate the active substance when capsule opacification occurs even years after the operation. The photochemical activation is preferably achieved by irradiating the precursor active substance with light. It is possible to select and predetermine the wavelength range of the irradiating light according to the type of the precursor active substance, for example whether it is an active substance immobilized by means of a photochemically cleavable linker or an active substance polymer. For example by using specific linker groups which can only be cleaved with light of a very special wavelength, it is possible to obtain a highly selective release of the active substance. Precursor active substances are preferably used which can be cleaved by irradiating them with UV light (100–400 nm), visible light (400–750 nm) or infrared light (750 nm–1000 µm).

From a therapeutic perspective it is advantageous when the active substance can be released by light of a very limited spectral range that covers no more than 50% and preferably no more than 25% of the visible spectral range. Hence it is possible to prevent a premature release by daylight during wound healing by wearing suitable glasses which filter out the relevant spectral range.

It is particularly advantageous when it is possible to induce the photochemical release of the active substance by a two-photon absorption of light of two identical or two different wavelengths. In this case the energy required for the photochemical release is advantageously in a wavelength range below the visible spectral range in the so-called ultraviolet range. Since the transmission of the natural cornea in the UV range is very low, it is not necessary to wear special glasses (see above) which would be coloured due to the required spectral properties and may therefore be undesirable for cosmetic reasons.

According to the invention it is preferable for the photochemical activation to require a relatively high energy which prevents an accidental premature release of the active substance in the absence of the intended photochemical activation. In particular a premature release by heat should be avoided.

The invention additionally comprises a process for the production of an ophthalmologic implant comprising the steps:

providing a polymeric material, immobilizing a chemical component on or/and in the polymeric material from which a pharmaceutical substance can be released by photochemical activation which preferably has a cytotoxic effect and in particular a toxic effect on epithelium and forming an ophthalmologic implant from the polymeric material.

The process for the production comprises two preferred variants. Thus the implant can be made of a polymeric material which already contains the chemical component or the implant can be firstly made from a non-doped material and the chemical component is then immobilized on the implant. This procedure enables for example the doping of conventional eye implants with chemical components to obtain implants according to the invention.

The invention additionally comprises the use of the ophthalmologic implant for the prophylaxis or treatment of capsule opacification after implantation of a synthetic lens.

Figure 2:
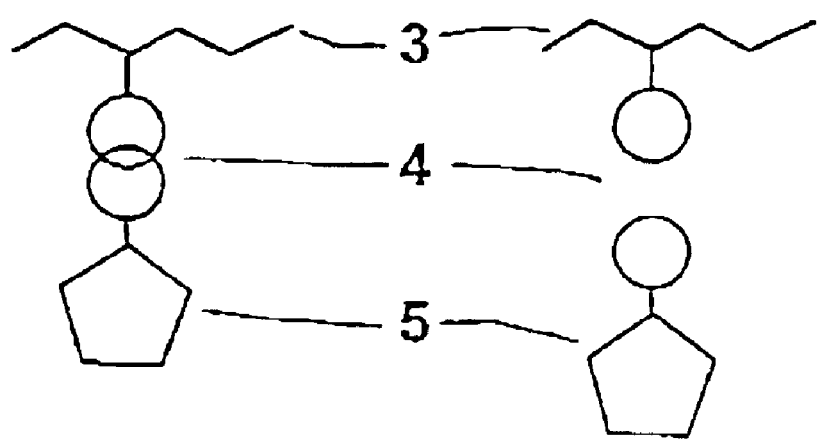
Figure 3:
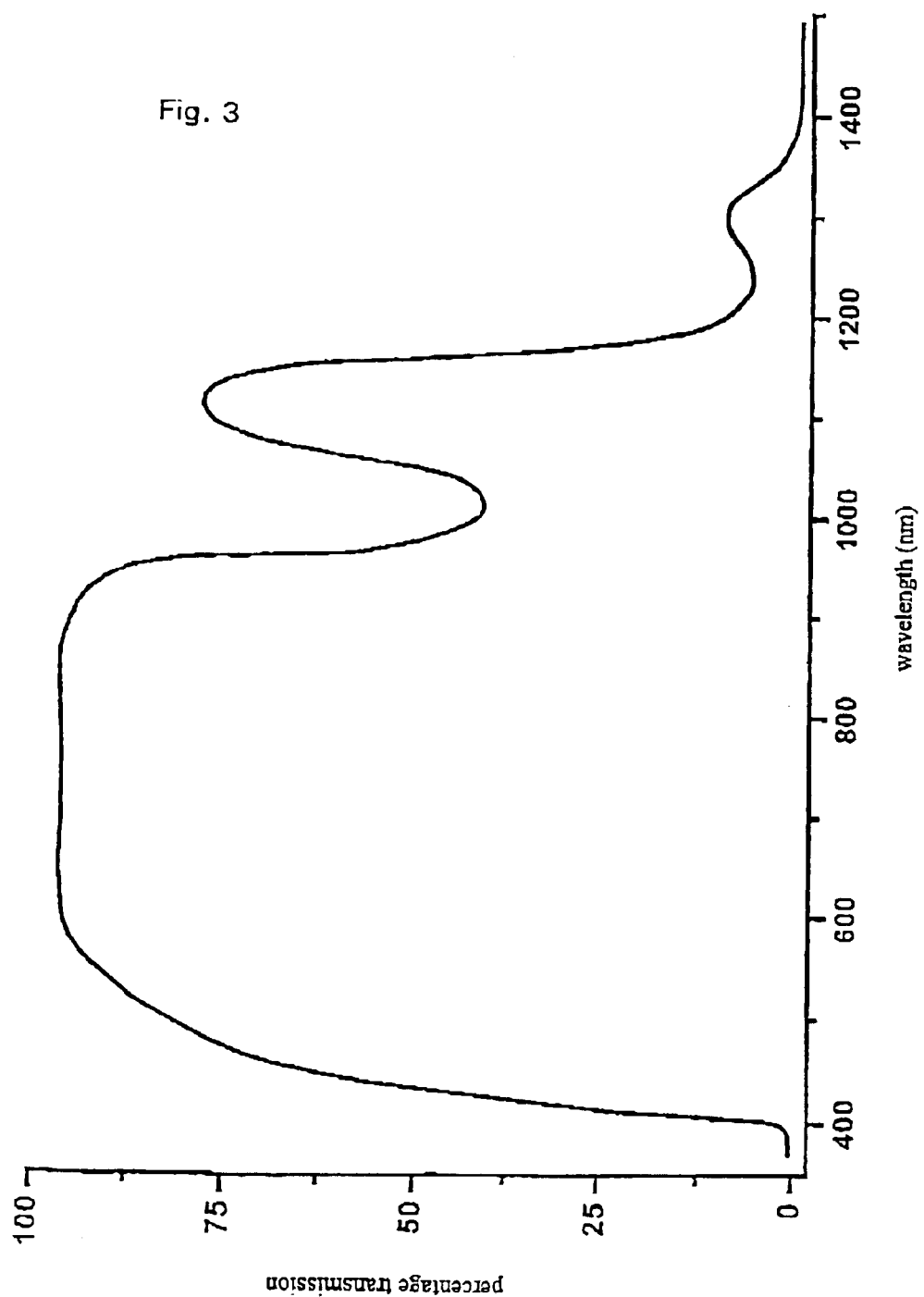
Figure 4:
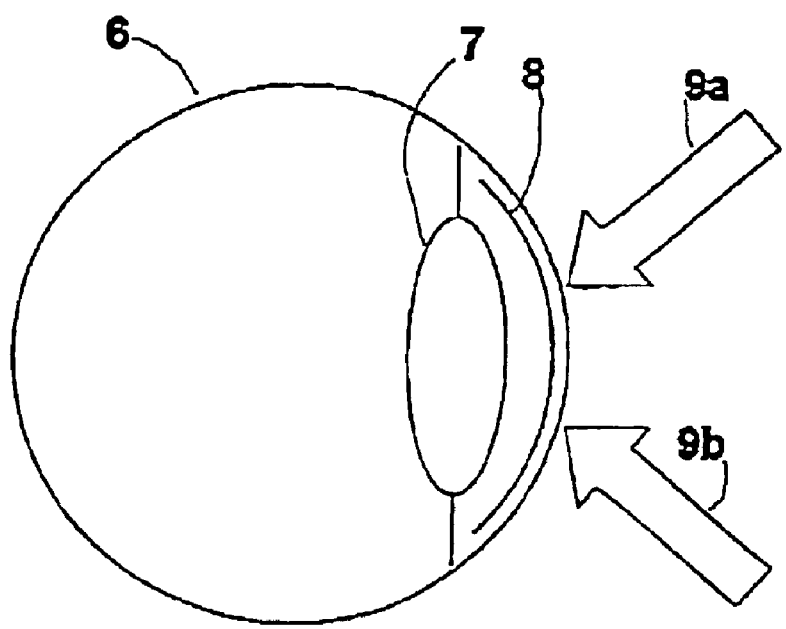

The invention is elucidated in more detail in the following by application examples and figures:

FIG. 1 shows an intraocular lens 1 and auxiliary equipment 2 for an intraocular lens in the form of a toroid;

FIG. 2 shows a schematic representation of the photochemically induced release of an active substance 5 bound to a polymeric structure 3 by means of photocleavable linker molecules 4;

FIG. 3 shows a typical absorption spectrum of the cornea of the eye with a high transmission in the visible and near infrared spectral range (400–1200 nm) and low transmission in the near UV range (<400 nm);

FIG. 4 shows a schematic representation of the eye 6 with an implanted polymeric intraocular lens 7, natural cornea 8 and light guide for a two-photon absorption to release the active substance from an intraocular lens according to the invention by means of two light rays 9a and 9b which have wavelengths in the range of high transmission by the cornea and overlap in the area of the implanted intraocular lens.

Some preferred embodiments of the invention and materials suitable for carrying out the invention are elucidated in the following:

1. Intraocular Lens and Auxiliary Equipment Therefor

The intraocular lens 1 can be manufactured completely from the polymer loaded with active substance. However, it is also alternatively possible to only provide a zone of a few micrometers thickness with a polymer loaded with the active substance e.g. by coating an intraocular lens. The active substance can be released particularly rapidly from this surface layer since only short diffusion paths are required.

The auxiliary equipment 2 of FIG. 1 consists for example of a ring-shaped body whose inner radius corresponds to the outer radius of the intraocular lens 1. The ring-shaped body which contains the active substance that is toxic for epithelial cells is optionally bound to the intraocular lens before implantation by gluing or it is co-implanted without a mechanical connection. In this manner conventional intraocular lenses can be provided with an active substance protection according to the invention during implantation. The advantage of this procedure is that no structural changes have to be made to the intraocular lens which could potentially reduce the long-term stability of the intraocular lens especially when large amounts of active substance have to be released. Another advantage is that an opacification of the material of the auxiliary equipment or an intentional colouration of the auxiliary equipment does not impair visual perception since the auxiliary equipment is preferably positioned peripherally in the capsule sac.

2. Polymeric Materials for Intraocular Lenses Containing Covalently Fixed Active Substances and Photocleavable Linkers A basic approach for incorporating a photochemically activatable active substance that is toxic for epithelial cells into an intraocular lens or the auxiliary equipment is described schematically and illustrated on the basis of an example in the following.

Step 1 Preparation of functionalized monomers e.g. coumarin-modified methacrylates or silicones Step 2 Preparation of functionalized active substances e.g. coumarin-modified 5-fluorouracil or mitomycin C Step 3 Coupling of the functionalized monomer to the functionalized active substance and optionally mixing with an additional monomer.

Step 4 Mixing with a further polymer without bound active substance.

Step 5 Cross-linking copolymerization

Step 6 Forming

Step 2 can be omitted when the active substance is itself used as a linker e.g. coumarin and its derivatives.

A polymerization can be included after step 2 in order to prepare active substance-linker conjugate oligomers.

Steps 3 and step 5 can also be carried out in the reverse order if necessary.

Step 4 can be omitted if a polymer blend is not necessary to adjust the mechanical properties of the intraocular lens or if it is intended to otherwise influence the processability of the polymeric material.

Step 5 can be omitted for polymers having a glass transition temperature $(T_g)>50°$ C.

Step 5 and step 6 can also be combined into one procedure.

Step 6 can be carried out as a cross-linking copolymerization. In this case the forming is preferably carried out during the polymerization.

2.1 Basic Materials

The known materials polymethylmethacrylate (PMMA) and silicone that are already used to produce commercially available intraocular lenses are employed as starting materials to produce the intraocular lens and the auxiliary equipment, respectively. Silicone lenses have been used to an increasing extent in recent years, since their foldability allows a microsurgical implantation.

2.2 Active Substances

All known cytotoxic or antineoplastic agents come into consideration as active substances. It is preferable to use the conventional ophthalmologic cytotoxic compounds 5-fluorouracil and mitomycin C which have a low molecular weight which ensures a rapid diffusion (minutes) from the intraocular lens into the chamber water. Eflorinithine, melphalcene, duanorubicin, coumarin and similar active substances also come into consideration. These compounds fulfil the chemical requirements for covalent immobilization in a particularly simple manner.

2.3 Photoactivatable Linkers

FIG. 2 shows the photochemically inducible cleavage of the active substance from the polymer by means of linker molecules. The left part of the figure refers to the state before photochemical activation in which the active substance is covalently bound via the linker molecule whereas the right part of the figure shows the state after photochemical activation in which the active substance is cleaved and released together with a linker molecule fragment.

Preferred photocleavable linker molecules are cinnamic acid derivatives due to their good synthetic properties and coumarin derivatives due to their photoreversible dimerization.

It is known that coumarins dimerize during a photochemically induced [2+2] cycloaddition (usually $\lambda_{max}>300$ nm). Experiments on low molecular polymer-bound coumarins showed that the photochemically induced dimerization is photochemically reversible (usually $\lambda_{max}<300$ nm). This reversible photochemical reaction has the advantage that the release of cytotoxic substances is induced by light in a dose-dependent manner and also that the photochemical reaction can be used during production to load the active substance. Release of undesired byproducts during photolysis is hitherto unknown. Cinnamic acid derivatives whose photodimerization is known, provide similar options.

3. Polymer Syntheses

Synthesis of polymers loaded with active substance.

3.1 Cross-dimerization of Coumarins

Cross-dimers (I) were prepared by photochemically cross-dimerizing (cf. ref.: Y. Chen, C.-F. Chou, J. Polym. Sci., Polym. Chem. 33, 2705 (1995)) OH- and $NH_2$-functionalized coumarin derivatives, respectively, with unsubstituted coumarin. They were purified by recrystallization and preparative high-pressure chromatography (HPLC).

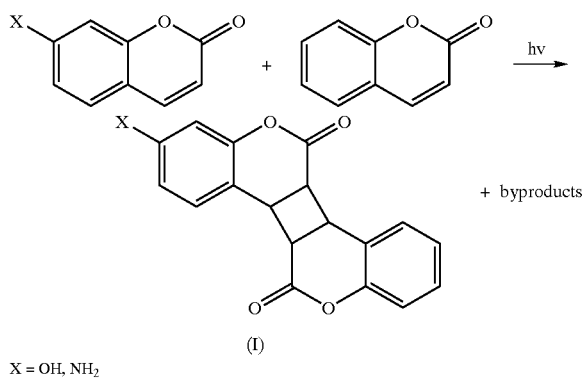

$X = OH, NH_2$

The cross-dimers (I) are reacted in a further reaction step with ω-unsaturated fatty acids, acrylate derivatives (e.g. acrylic acid chloride) or methacrylate derivatives (e.g.

metacrylic acid chloride) to form corresponding esters and amides (II).

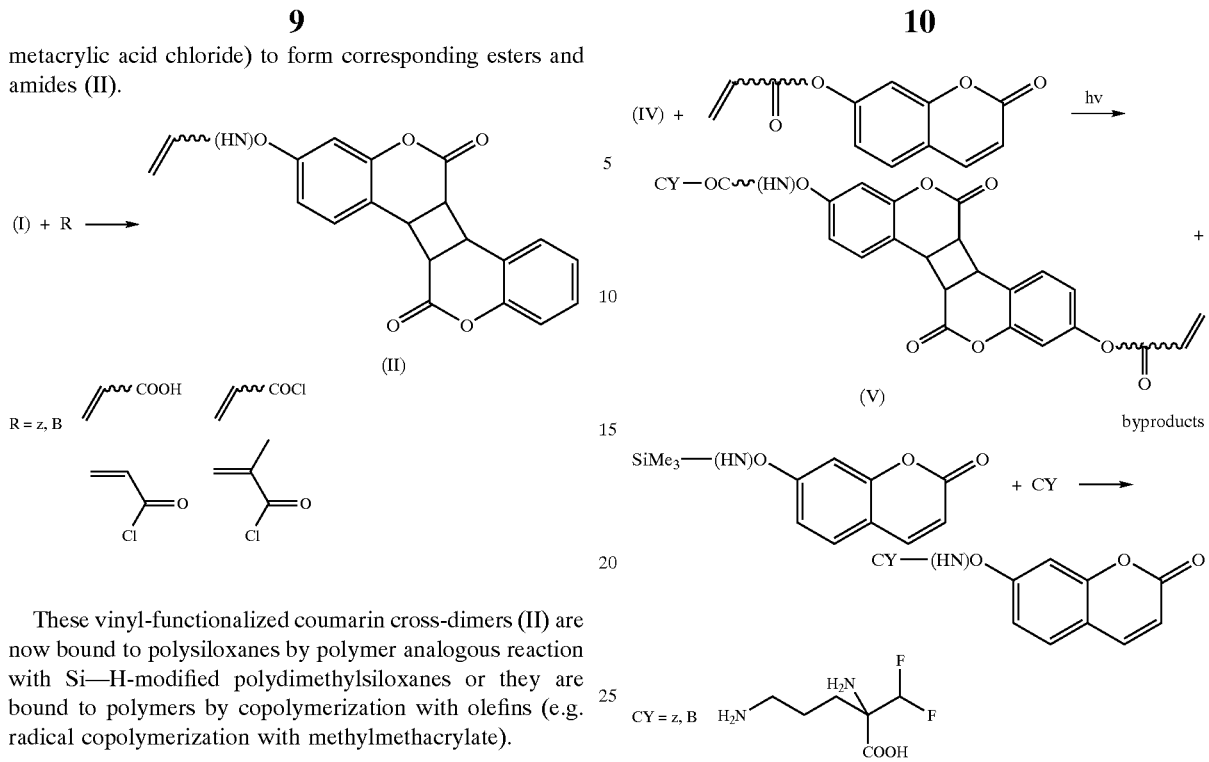

These vinyl-functionalized coumarin cross-dimers (II) are now bound to polysiloxanes by polymer analogous reaction with Si—H-modified polydimethylsiloxanes or they are bound to polymers by copolymerization with olefins (e.g. radical copolymerization with methylmethacrylate).

3.2 Reaction with Anhydrides

OH- and $NH_2$-functionalized coumarin derivatives, respectively, are firstly reacted with dicarboxylic acid anhydrides and silylated. Subsequently $NH_2$-containing cytotoxic agents (e.g. eflornithine) are bound by amidation with the free silylated carboxylic acid group of the coumarin derivative.

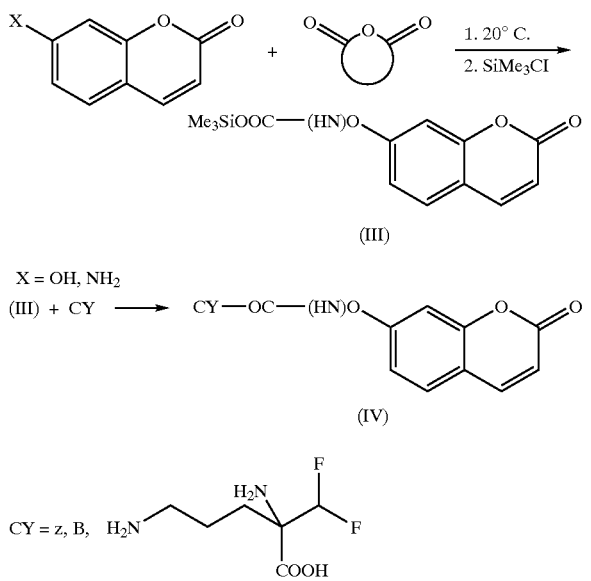

Polydimethylsiloxanes and polymethacrylates, respectively, and polyacrylates that are loaded with active substance can be prepared by photochemical cross-dimerization with a vinyl-functionalized coumarin derivative and subsequent polymer analogous reaction or copolymerization (cf. 3.1).

3.3 Reaction with Silylated Coumarin Derivatives

Amino-functionalized coumarin derivatives are firstly silylated at the amino function and subsequently linked with suitable cytotoxic agents e.g. eflornithines by an amidation reaction.

Polydimethylsiloxanes and polymethacrylates, respectively, and polyacrylates that are loaded with active substance can be prepared by photochemical cross-dimerization with a vinyl-functionalized coumarin derivative (cf. 3.2) and subsequent polymer analogous reaction or copolymerization (cf. 3.1).

4. Production of Intraocular Lenses Based on Polymeric Materials with Dispersed Medicinal Substances When polymethylmethacrylate (PMMA) is used as the polymeric material it is possible to alternatively incorporate a precursor of an active substance by diffusion into the material. For this purpose the PMMA sample is softened with a swelling agent and brought into contact with a liquid containing the precursor of the active substance in a dissolved form. The precursor of the active substance diffuses into the PMMA matrix. After removing the solvent, an intraocular lens is obtained with an incorporated depot of an active substance precursor in a macromolecular form which is dissolved or nanodispersed. The active substance can be released from the active substance precursor by photochemical cleavage and can then diffuse out of the intraocular lens.

5. Photochemical Release of the Medicinal Substance by Two-photon Absorption

FIG. 4 shows schematically an eye 6 with an UV-absorbing cornea 8 and implanted intraocular lens 7. The intraocular lens 7 contains the active substance which is to be released. In order to eliminate lens epithelial cells after completion of wound healing (secondary cataract treatment), the eye is irradiated with two laser beams 9a and 9b with different wavelengths at different angles. The two laser beams 9a and 9b which penetrate through the cornea are focussed by lenses in such a manner that they are superimposed in a small volume in or on the intraocular lens loaded with the active substance. In this manner photochemical cleavage of the linker molecules by two-photon absorption is induced in the volume of intersection.

A spatially sharply defined photochemical cleavage of the linker molecules can be triggered in this manner by a suitable combination of wavelengths in the overlapping region of the two laser beams.

For an application in the eye it is of course undesirable if daylight already leads to a release of the medicinal substance. The cornea has a poor transmission for wavelengths of less than 400 nm. A transmission of more than 90% is achieved between 500 nm and 900 nm (cf. e.g. W. J. Geeraets, E. R. Berry: Ocular spectral characteristics as related to hazards from lasers and other light sources. Am. J. Ophthalmol. 66 (1968) 15–20).

The advantage of two-photon activation is that the photochemically desired reaction can be induced behind the cornea which absorbs the required primary wavelength. However, a disadvantage is that the absorption coefficient for two-photon absorption is several orders of magnitude below that for one-photon absorption. Thus much higher energies are necessary at the site of the desired photochemistry than for a comparable one-photon reaction. However, this problem can be solved with the aid of the described optical system in which focussed laser beams are used which are for example guided by a light guide and are superimposed at an angle of for example 90°. As a result of the strong focussing the beams widen substantially behind the site of the reaction such that tolerable intensities are not exceeded in the plane of the periphery of the retina.

What is claimed is:

1. Ophthalmologic implant for the prophylaxis or treatment of capsule opacification after implantation of a synthetic lens, the implant comprising a polymeric material and, at least in certain areas of the polymeric material, a chemical component in an immobilized form, from which chemical component a pharmaceutically active substance will be released upon photochemical activation, wherein the photochemical activation is achieved by a two-photon absorption.

2. Ophthalmologic implant as claimed in claim 1, wherein the implant is an intraocular lens.

3. Ophthalmologic implant as claimed in claim 1, wherein the implant is an auxiliary equipment for intraocular lenses.

4. Ophthalmologic implant as claimed in claim 1, wherein the active substance has a cytotoxic effect.

5. Ophthalmologic implant as claimed in claim 1, wherein the active substance has an antibiotic, an antiinflammatory, an antimicrobial, an antiviral or/and a fungicidal effect.

6. Ophthalmologic implant as claimed in claim 1, wherein the active substance is a corticosteroid, a non-steroidal antiinflammatory agent or an anti-fibroblast growth factor or/and an active substance which inhibits proliferative vitreoretinopathy or tissue fibrosis.

7. Ophthalmologic implant as claimed in claim 1, wherein the active substance is covalently bound to the polymeric material.

8. Ophthalmologic implant as claimed in claim 1, wherein the active substance is coupled to the polymeric material via photochemically cleavable linker molecules.

9. Ophthalmologic implant as claimed in claim 8, wherein the linker molecules are selected from the group comprising cinnamic acid, coumarin and derivatives thereof.

10. Ophthalmologic implant as claimed in claim 1, wherein the active substance or/and a precursor of the active substance is or are embedded in the polymeric material.

11. Ophthalmologic implant as claimed in claim 1, wherein a precursor of the active substance is embedded in a finely dispersed form in the polymeric material.

12. Ophthalmologic implant as claimed in claim 11, wherein the average particle size of the dispersed precursor of the active substance is $\leq 1$ μm.

13. Ophthalmologic implant as claimed in claim 1, wherein the polymeric material comprises a precursor of an active substance in an oligomeric or polymeric form.

14. Ophthalmologic implant as claimed in claim 1, wherein the polymeric material comprises a precursor of an active substance in the form of macromolecular conjugates.

15. Ophthalmologic implant as claimed in claim 1, wherein the active substance is released by irradiation with light in a spectral range which covers not more than 50% of the visible spectral range.

* * * * *